United States Patent

Jensen et al.

[11] Patent Number: 5,807,378
[45] Date of Patent: Sep. 15, 1998

[54] SURGICAL MANIPULATOR FOR A TELEROBOTIC SYSTEM

[75] Inventors: Joel F. Jensen, Redwood City; John W. Hill, Palo Alto, both of Calif.

[73] Assignee: SRI International, Menlo Park, Calif.

[21] Appl. No.: 944,362

[22] Filed: Oct. 6, 1997

Related U.S. Application Data

[63] Continuation of Ser. No. 487,020, Jun. 7, 1995, abandoned.

[51] Int. Cl.$^6$ .................................................. A61B 17/00
[52] U.S. Cl. ............................ 606/1; 606/130; 473/316; 473/319
[58] Field of Search ............................... 606/1, 130, 205, 606/206, 207; 605/905; 901/18, 21, 23, 24, 25, 41, 32, 38; 279/93, 94; 414/744.2, 744.3; 403/349, 348, 316

[56] References Cited

U.S. PATENT DOCUMENTS

| | | |
|---|---|---|
| 1,418,184 | 5/1922 | Trunic . |
| 2,815,697 | 12/1957 | Saunders-Singer .......................... 88/40 |
| 2,901,258 | 8/1959 | Brandafi . |
| 3,145,333 | 8/1964 | Pardini et al. . |
| 3,463,329 | 8/1969 | Gartner ....................................... 214/1 |
| 3,818,125 | 6/1974 | Butterfield . |
| 3,921,445 | 11/1975 | Hill et al. . |
| 3,923,166 | 12/1975 | Fletcher et al. . |

(List continued on next page.)

FOREIGN PATENT DOCUMENTS

| | | |
|---|---|---|
| 0 239 409 | 9/1987 | European Pat. Off. ........... A61F 9/00 |
| 0 291 292 | 11/1988 | European Pat. Off. ........ F16H 21/44 |
| 0 595 291 | 5/1994 | European Pat. Off. ........... B25J 9/10 |
| 8 600 852 | 1/1986 | France . |
| 3 806 190 | 9/1988 | Germany . |
| 482439 | 1/1970 | Switzerland . |
| 2 040 134 | 8/1980 | United Kingdom . |
| 2117732 | 10/1983 | United Kingdom ............... B25J 9/00 |

OTHER PUBLICATIONS

Alexander Arthur D., III, "Impacts of Telemation on Modern Society," (NASA, Ames Research Center, Advanced Concepts and Missions Div., Moffett Field, California) in *Symposium on Theory and Practise of Robots and Manipulators*, 1st Udine, Italy, Sep. 5–8, 1973, Preprints, (A74–16130 04–05) Udine, Italy, Internation Center for Mechanical Sciences, 1973, pp. 122–136.

Bejczy A. K. et al., "Controlling Remote Manipulators Through Kinesthetic Coupling," 1983, *Computers in Mechanical Engineering*, pp. 48–60.

(List continued on next page.)

*Primary Examiner*—Michael Powell Buiz
*Assistant Examiner*—Daphja Shai
*Attorney, Agent, or Firm*—Townsend and Townsend and Crew LLP

[57] ABSTRACT

The invention is directed to manipulator assembly (2) for holding and manipulating a surgical instrument (14) in a telerobotic system. The assembly comprises a base (6) fixable by passive or power driven positioning devices to a surface, such as an operating table, and an instrument holder (4) movably mounted on the base. The instrument holder comprises a chassis (6) and an instrument support (70) movably mounted on the body and having an interface engageable with the surgical instrument to releasably mount the instrument to the instrument holder. A drive assembly (7) is operatively coupled to the instrument holder for providing the instrument with at least two degrees of freedom. The instrument holder is separable from the base and the drive assembly so that the holder can be sterilized. The assembly further includes a force sensing element (52) mounted distal to the holder and the drive assembly for detecting forces exerted on the surgical instrument and providing feedback to the surgeon. The assembly is attached to a remote center positioner (300) for constraining the instrument to rotate about a point coincident with the entry incision and an inclinometer (350) for preventing gravitational forces acting on the system's mechanisms from being felt by the surgeon.

8 Claims, 9 Drawing Sheets

U.S. PATENT DOCUMENTS

| | | |
|---|---|---|
| 3,934,201 | 1/1976 | Majefski . |
| 4,113,115 | 9/1978 | Yoshio ..................................... 901/38 |
| 4,260,319 | 4/1981 | Motoda et al. . |
| 4,264,266 | 4/1981 | Trechsel ................................... 901/21 |
| 4,349,837 | 9/1982 | Hinds . |
| 4,419,041 | 12/1983 | Rose ........................................ 901/25 |
| 4,510,574 | 4/1985 | Guittet et al. . |
| 4,562,463 | 12/1985 | Lipton . |
| 4,582,067 | 4/1986 | Silverstein et al. . |
| 4,583,117 | 4/1986 | Lipton et al. . |
| 4,636,138 | 1/1987 | Gorman ................................... 901/21 |
| 4,651,201 | 3/1987 | Schoolman . |
| 4,744,363 | 5/1988 | Hasson . |
| 4,750,475 | 6/1988 | Yoshihashi . |
| 4,751,925 | 6/1988 | Tontarra . |
| 4,808,898 | 2/1989 | Pearson . |
| 4,837,734 | 6/1989 | Ichikawa et al. . |
| 4,855,822 | 8/1989 | Narendra et al. . |
| 4,862,873 | 9/1989 | Yajima et al. . |
| 4,873,572 | 10/1989 | Miyazaki et al. . |
| 4,899,730 | 2/1990 | Stennert et al. . |
| 4,922,338 | 5/1990 | Arpino . |
| 4,941,106 | 7/1990 | Kireger . |
| 4,942,539 | 7/1990 | McGee et al. . |
| 4,947,702 | 8/1990 | Kato ........................................ 901/21 |
| 5,002,418 | 3/1991 | McCown et al. . |
| 5,020,933 | 6/1991 | Salvestro et al. . |
| 5,045,936 | 9/1991 | Lobb et al. . |
| 5,060,532 | 10/1991 | Barker ..................................... 74/479 |
| 5,062,761 | 11/1991 | Glachet ................................... 901/25 |
| 5,078,140 | 1/1992 | Kwoh ..................................... 128/653 |
| 5,096,236 | 3/1992 | Thöny . |
| 5,141,519 | 8/1992 | Smith et al. . |
| 5,142,930 | 9/1992 | Allen et al. . |
| 5,219,351 | 6/1993 | Teubner et al. ......................... 101/130 |
| 5,236,432 | 8/1993 | Matsen, III et al. . |
| 5,253,706 | 10/1993 | Reid . |
| 5,257,998 | 11/1993 | Ota et al. ................................ 606/130 |
| 5,264,266 | 11/1993 | Yokoyama et al. . |
| 5,273,039 | 12/1993 | Fujiwara et al. ........................ 606/130 |
| 5,279,309 | 1/1994 | Taylor et al. . |
| 5,281,220 | 1/1994 | Blake, III . |
| 5,284,130 | 2/1994 | Ratliff . |
| 5,325,866 | 7/1994 | Krzyzanowski . |
| 5,397,323 | 3/1995 | Taylor et al. . |
| 5,425,528 | 6/1995 | Rains et al. . |
| 5,441,505 | 8/1995 | Nakamura . |
| 5,474,566 | 12/1995 | Alesi et al. ............................. 606/205 |
| 5,480,409 | 1/1996 | Riza ........................................ 606/205 |
| 5,636,138 | 6/1997 | Gilbert et al. . |

OTHER PUBLICATIONS

Fisher et al., "Virtual Interface Environment," Oct. 1986, *Proceedings IEEE/AIAA 7th Digital Avionics Systems Conference*, Fort Worth, Texas, pp. 346–350.

Held Richard et al., "Telepresence, Time Delay and Adaptation," in *NASA, Ames Research Center, Spatial Displays and Spatial Instruments Proceedings of a Conference Sponsored by Nasa Ames Research Center and The School of Optometry, University of California*, Jul. 1989, pp. 28–1 through 28–16.

Kim et al., "A Helmet Mounted Display For Telerobotics," 1988, 33 IEEE Computer Society International Conference, California, pp. 543–547.

Jau B. M., "Anthropomorphic Remoter Manipulator", Apr. 1991, *NASA Tech Briefs*, NASA's Jet Propulsion Laboratory, Pasadena, California, p. 92.

Matsushima K., "Servo Micro Manipulator Tiny Micro Mark–1," *4th Symposium on Theory and Practise of Robots and Manipulators*, pp. 193–201.

Richter R., "Telesurgery May Bridge Future Gaps," 1988, *Times Tribune*, Sunday, Jan. 24, pp. A–1 and A–16.

Spain E. H., "Stereo Advantage for a Peg–In–Hole Task Using Force–Feedback Manipulator," 1990, *Stereoscopic Displays and Applications*, pp. 244–254.

Tachi et al., "Tele–Existence Master Slave System for Remote Manipulation," 1990, *Proceedings of the 29th Conference on Decision and Control*, vol. 1 of 6, pp. 85–90.

Blue Cross Magazine Perspective, "Another Pair of Hands for Sugeon?", First Quarter 1972, *The Blue Cross Magazine Perspective*, p. 27.

Taylor, Russell H., et al., "A Telerobotic Assistant for Laparoscopic Surgery", *IEEE Engineering in Medicine and Biology*, May/Jun. 1995, pp. 279–288.

Ng, W.S. et al., "Robotic Surgery, A First–Hand Experience in Transurethral Resection of the Prostate", *IEEE Engineering in Medicine and Biology*, Mar. 1993, pp. 120–125.

Taubes, Gary, "Surgery in Cyberspace", *Discover*, Dec. '94, pp. 85–92.

Computer Motion Inc., "AESOP Automated Endoscopic System for Optimal Positioning", advertisement.

Asada, Haruhiko et al., "Development of a Direct–Drive Arm Using High Torque Brushless Motors", pp. 583–599.

Kazerooni, H., "Design and Analysis of the Statically Balanced Direct–Drive Robot Manipulator", *Robotics & Computer–Integrated Manuf.*, vol. 5, No. 4, pp. 287–293, 1989.

Guerrouad, Aicha et al., "SMOS: Stereotaxical Microtelemanipulator for Ocular Surgery", *IEEE Engineering in Medicine & Biology Soc.*, 11th Ann. Int'l Conf., 0879, CH2770–689/0879.

Trevelyan, James P., et al., "Motion Control for a Sheep Shearing Robot", pp. 175–190.

SURGICAL MANIPULATOR FOR A TELEROBOTIC SYSTEM

This is a Continuation of U.S. patent application Ser. No. 08/487,020, filed Jun. 7, 1995, now abandoned, the disclosure of which is incorporated by reference.

BACKGROUND OF THE INVENTION

This invention relates to surgical manipulators and more particularly to robotically-assisted apparatus for use in surgery.

In standard laparoscopic surgery, a patient's abdomen is insufflated with gas, and trocar sleeves are passed through small (approximately ½ inch) incisions to provide entry ports for laparoscopic surgical instruments. The laparoscopic surgical instruments generally include a laparoscope for viewing the surgical field, and working tools such as clamps, graspers, scissors, staplers, and needle holders. The working tools are similar to those used in conventional (open) surgery, except that the working end of each tool is separated from its handle by an approximately 12-inch long extension tube. To perform surgical procedures, the surgeon passes instruments through the trocar sleeves and manipulates them inside the abdomen by sliding them in and out through the sleeves, rotating them in the sleeves, levering (i.e., pivoting) the sleeves in the abdominal wall and actuating end effectors on the distal end of the instruments.

In robotically-assisted and telerobotic surgery (both open and endoscopic procedures), the position of the surgical instruments is controlled by servo motors rather than directly by hand or with fixed clamps. The servo motors follow the motions of a surgeon's hands as he/she manipulates input control devices and views the operation via a displayed image from a location that may be remote from the patient. The servo motors are typically part of an electromechanical device or surgical manipulator that supports and controls the surgical instruments that have been introduced directly into an open surgical site or through trocar sleeves into a body cavity, such as the patient's abdomen. During the operation, the surgical manipulator provides mechanical actuation and control of a variety of surgical instruments, such as tissue graspers, needle drivers, etc, that each perform various functions for the surgeon, i.e., holding or driving a needle, grasping a blood vessel or dissecting tissue.

This new method of performing telesurgery through remote manipulation will create many new challenges. One such challenge is transmitting position, force, and tactile sensations from the surgical instrument back to the surgeon's hands as he/she operates the telerobotic system. Unlike other techniques of remote manipulation, telesurgery can give the surgeon the feeling that he/she is manipulating the surgical instruments directly by hand. For example, when the instrument engages a tissue structure or organ within the patient, the system should be capable of detecting the reaction force against the instrument and transmitting this force to the input control devices. In this manner, the surgeon can see the instrument contacting the tissue structure on the displayed image and directly feel the pressure from this contact on the input control devices. Providing the appropriate feedback, however, can be problematic because of other forces acting on the system, such as friction within the telerobotic mechanisms, gravity and inertial forces acting on the surgical manipulator or forces exerted on a trocar sleeve by the surgical incision.

In addition, to enable effective telesurgery, the manipulator must be highly responsive and must be able to accurately follow even the most rapid hand motions that a surgeon frequently uses in performing surgical procedures. To achieve this rapid and responsive performance, a telerobotic servo system must be designed to have an appropriately high servo bandwidth which requires that the manipulator be designed to have low inertia and to employ drive motors with relatively low ratio gear or pulley couplings.

Another challenge with telesurgery results from the fact that a portion of the electromechanical surgical manipulator will be in direct contact with the surgical instruments, and will also be positioned adjacent the operation site. Accordingly, the surgical manipulator may become contaminated during surgery and is typically disposed of or sterilized between operations. Of course, from a cost perspective, it would be preferable to sterilize the device. However, the servo motors, sensors and electrical connections that are necessary to robotically control the motors typically cannot be sterilized using conventional methods, e.g., steam, heat and pressure or chemicals, because they would be damaged or destroyed in the sterilization process.

What is needed, therefore, is a robotically-assisted apparatus for holding and manipulating surgical instruments by remote control. The apparatus should be configured for easy sterilization so that it can be reused after it has been contaminated during an operation. The apparatus should be further capable of providing the surgeon with the appropriate feedback from forces transmitted to and from the surgical instrument during the telerobotic operation and it should be configured to compensate for gravitational forces acting on the apparatus so that these forces are not felt by the surgeon. In addition, the apparatus must be highly responsive and must be able to accurately follow even the most rapid hand motions that a surgeon frequently uses in performing surgical procedures.

SUMMARY OF THE INVENTION

According to the invention, an apparatus is provided for holding and manipulating a surgical instrument during conventional open surgery or endoscopic procedures, such as laparoscopy. The apparatus comprises a support base fixable by means of various passive or power driven positioning devices to a surface, such as an operating table, and an instrument holder movably mounted on the base. The instrument holder comprises a body and an instrument support movably coupled to the body and having an interface engageable with the surgical instrument to releasably mount the instrument to the instrument holder. A drive assembly is operatively coupled to the instrument holder for providing the instrument with at least two degrees of freedom. The drive assembly includes a first drive for moving the instrument support and a second drive for moving the instrument holder relative to the support base. The apparatus includes means for removably coupling the instrument holder from the base and the drive assembly so that the holder can be separated from the rest of the device and sterilized after a surgical procedure.

In a specific configuration, the support base includes a frame with distal and proximal support members and a pair of shafts rotatably mounted within the support members. The instrument holder is slidably mounted on the support shafts for axial movement of the instrument. In addition, the shafts are each coupled to a drive motor for providing the instrument with second and third degrees of freedom, e.g., rotation and end effector actuation. The drive motors are coupled to the proximal support member so that they will not be contaminated during surgery. The rotatable shafts can be removed by sliding them upward and out of engagement with their lower bearings and the instrument holder so that the instrument holder can be easily removed from the support base for sterilization. The lower portion of the support base (including the distal support member) may also be sterilized to decontaminate those parts that have contacted the instrument holder. In this manner, the surgical manipulator can be easily sterilized after a surgical procedure without damaging the servo motors or the electrical connections required for the telerobotic system.

The support base further comprises a sleeve, such as a cannula or trocar sleeve, mounted on the distal support member. The sleeve has an axial passage for receiving the instrument therethrough and a force sensing element mounted within the axial passage near the distal end of the sleeve. The force sensing element is configured to detect lateral forces exerted on the element by the distal portion of the instrument during surgery. Since the force sensing element is mounted distal to the remainder of the apparatus, it is undisturbed by forces that may be exerted on the cannula by the surgical incision or by gravity and inertial forces that act on the instrument holder. When supported by a positioning device, the surgical manipulator can be used with an inclinometer to determine the true orientation of the instrument holder with respect to the direction of the local gravitational field. Use of the inclinometer and force sensors with the manipulator facilitates the design of a telerobotic system in which the surgeon will directly sense the forces acting against the end of the instrument, unaffected by extraneous forces acting on the telerobotic mechanism. In other words, the surgeon will feel as if his/her hands are holding the instrument at the point in which the instrument contacts the force sensing element.

The invention is particularly useful for holding and manipulating a surgical instrument having an end effector, such as a pair of jaws, coupled to the distal end of the instrument shaft. To that end, the instrument holder further includes an actuator driver having an interface engageable with an end effector actuator on the instrument. The actuator driver includes a coupling that connects the driver to the drive assembly for axially moving a portion of the driver relative to the support base, thereby actuating the end effector of the instrument. In a preferred configuration, the coupling is a concentric helical actuator that translates rotation from a drive motor into axial movement of the end effector actuator. Because of the symmetrical design of the helical actuator, the actuation force applied by the drive motor will not generate any effective side loads on the instrument, which avoids frictional coupling with other degrees of freedom such as axial movement and rotation of the instrument.

Other features and advantages of the invention will appear from the following description in which the preferred embodiment has been set forth in detail in conjunction with the accompanying drawings.

DESCRIPTION OF THE PREFERRED EMBODIMENTS

Figure 1:
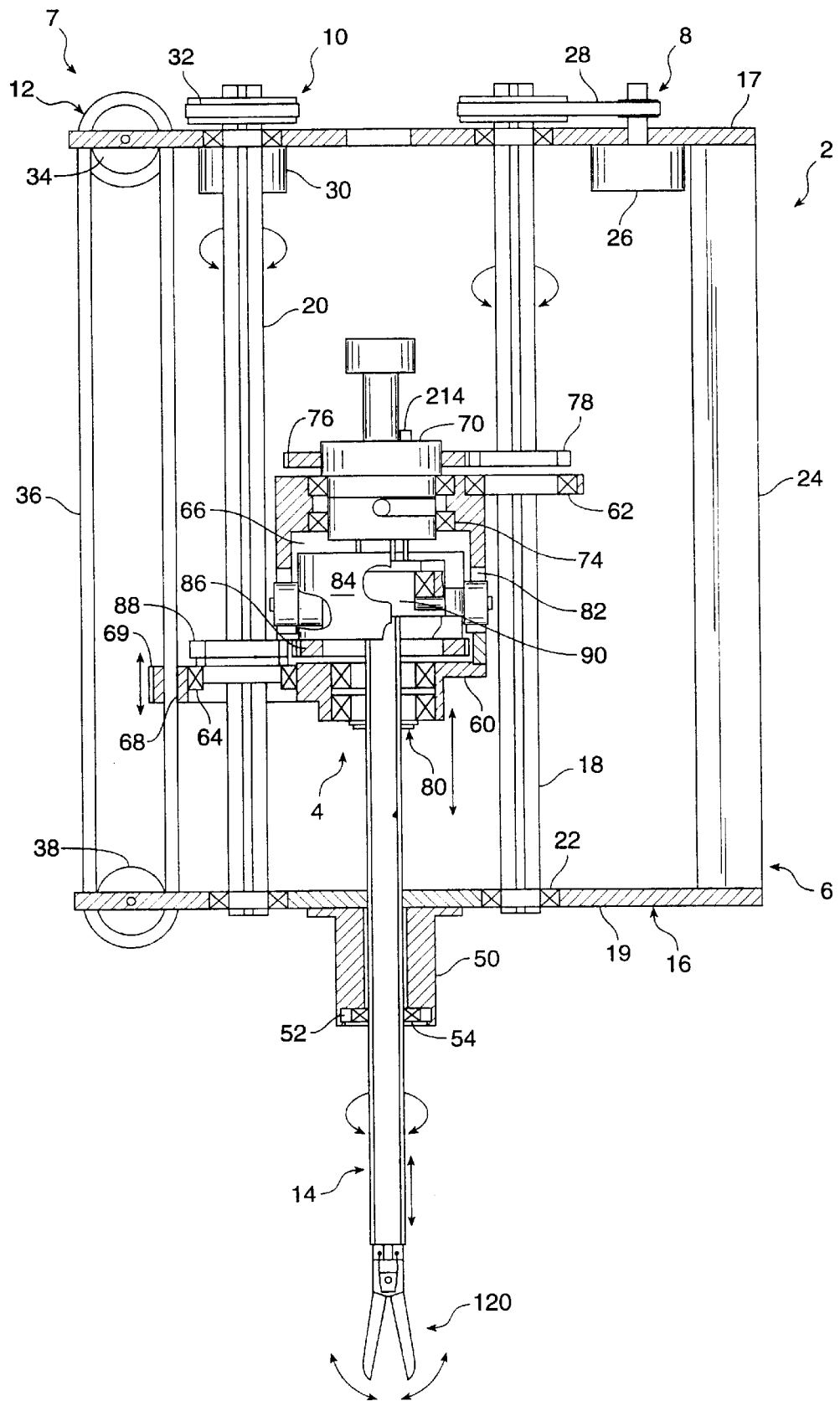
FIG. 1 is a partial sectional elevational view of a robotic endoscopic surgical instrument mounted to a manipulator assembly according to the present invention.

Referring to the drawings in detail, wherein like numerals indicate like elements, a manipulator assembly 2 is illustrated according to the principles of the invention. Manipulator assembly 2 generally includes an instrument holder 4 removably mounted to a base 6 and a drive assembly 7 for manipulating a surgical instrument 14 releasably coupled to instrument holder 4.

Referring to FIG. 1, base 6 comprises a frame 16 having proximal and distal elongate support members 17, 19 and first and second ball-spline shafts 18, 20 rotatably coupled to support members 17, 19 via bearings 22. Frame 16 further includes a support bracket 24 for attaching manipulator assembly 2 to a remote center positioner 300, as discussed in more detail below (see FIG. 9). Drive assembly 7 comprises first, second and third drives 8, 10, 12, which are mounted to frame 16 and configured to provide three degrees of freedom to surgical instrument 14. In the preferred embodiment, first drive 8 rotates instrument 14 around its own axis, second drive 10 actuates an end effector 120 on the distal end of instrument 14 and third drive 12 axially displaces instrument 14 with respect to frame 16. Of course, it will be readily recognized by those skilled in the art that other configurations are possible. For example, assembly 2 may include additional drives for providing additional degrees of freedom to surgical instrument 14, such as rotation and flexion of an instrument wrist.

First drive 8 comprises a rotation drive motor 26 fixed to frame 16 and coupled to first shaft 18 by a drive belt 28 for rotating first shaft 18 with respect to frame 16. Second drive 10 comprises a gripper drive motor 30 fixed to frame 16 and coupled to second shaft 20 by a drive belt 32 for rotating second shaft 20 with respect to frame 16. Third drive 12 comprises a vertical drive motor 34 coupled to instrument holder 4 via a drive belt 36 and two pulleys 38 for axially displacing instrument holder 4 with respect to frame 16. Drive motors 26, 30, 34 are preferably coupled to a controller mechanism via servo-control electronics (not shown) to form a telerobotic system for operating surgical instrument 14 by remote control. The drive motors follow the motions of a surgeon's hands as he/she manipulates input control devices at a location that may be remote from the patient. A suitable telerobotic system for controlling the drive motors is described in commonly assigned co-pending application Ser. No. 07/823,932 filed Jan. 21, 1992 TELEOPERATOR SYSTEM AND METHOD WITH TELEPRESENCE, which is incorporated herein by reference.

The above described telerobotic servo system preferably has a servo bandwidth with a 3 dB cut off frequency of at least 10 hz so that the system can quickly and accurately respond to the rapid hand motions used by the surgeon. To operate effectively with this system, instrument holder 4 has a relatively low inertia and drive motors 26, 30, 34 have relatively low ratio gear or pulley couplings.

In a specific embodiment, surgical instrument 14 is an endoscopic instrument configured for introduction through a percutaneous penetration into a body cavity, such as the abdominal or thoracic cavity. In this embodiment, manipulator assembly 2 supports a cannula 50 on distal support member 19 of frame 16 for placement in the entry incision during an endoscopic surgical procedure (note that cannula 50 is illustrated schematically in FIG. 1 and will typically be much longer). Cannula 50 is preferably a conventional gas sealing trocar sleeve adapted for laparoscopic surgery, such as colon resection and Nissen fundoplication.

As shown in FIG. 1, cannula 50 preferably includes a force sensing element 52, such as a strain gauge or force-sensing resistor, mounted to an annular bearing 54 within cannula 50. Bearing 54 supports instrument 14 during surgery, allowing the instrument to rotate and move axially through the central bore of bearing 54. Bearing 54 transmits lateral forces exerted by the instrument 14 to force sensing element 52, which is operably connected to the controller mechanism for transmitting these forces to the input control devices (not shown) held by the surgeon in the telerobotic system. In this manner, forces acting on instrument 14 can be detected without disturbances from forces acting on cannula 50, such as the tissue surrounding the surgical incision, or by gravity and inertial forces acting on manipulator assembly 2. This facilitates the use of manipulator assembly in a robotic system because the surgeon will directly sense the forces acting against the end of instrument 14. Of course, the gravitational forces acting on the distal end of instrument 14 will also be detected by force sensing element 52. However, these forces would also be sensed by the surgeon during direct manipulation of the instrument.

As shown in FIG. 1, instrument holder 4 comprises a chassis 60 mounted on shafts 18, 20 via ball-spline bearings 62, 64 so that chassis 60 may move axially with respect to shafts 18, 20, but is prevented from rotating with shafts 18, 20. Chassis 60 is preferably constructed of a material that will withstand exposure to high temperature sterilization processes, such as stainless steel, so that chassis 60 can be sterilized after a surgical procedure. Chassis 60 includes a central cavity 66 for receiving surgical instrument 14 and an arm 68 laterally extending from chassis 60. Arm 68 is fixed to drive belt 36 so that rotation of drive belt 36 moves instrument holder 4 in the axial direction along shafts 18, 20.

Figure 1A:
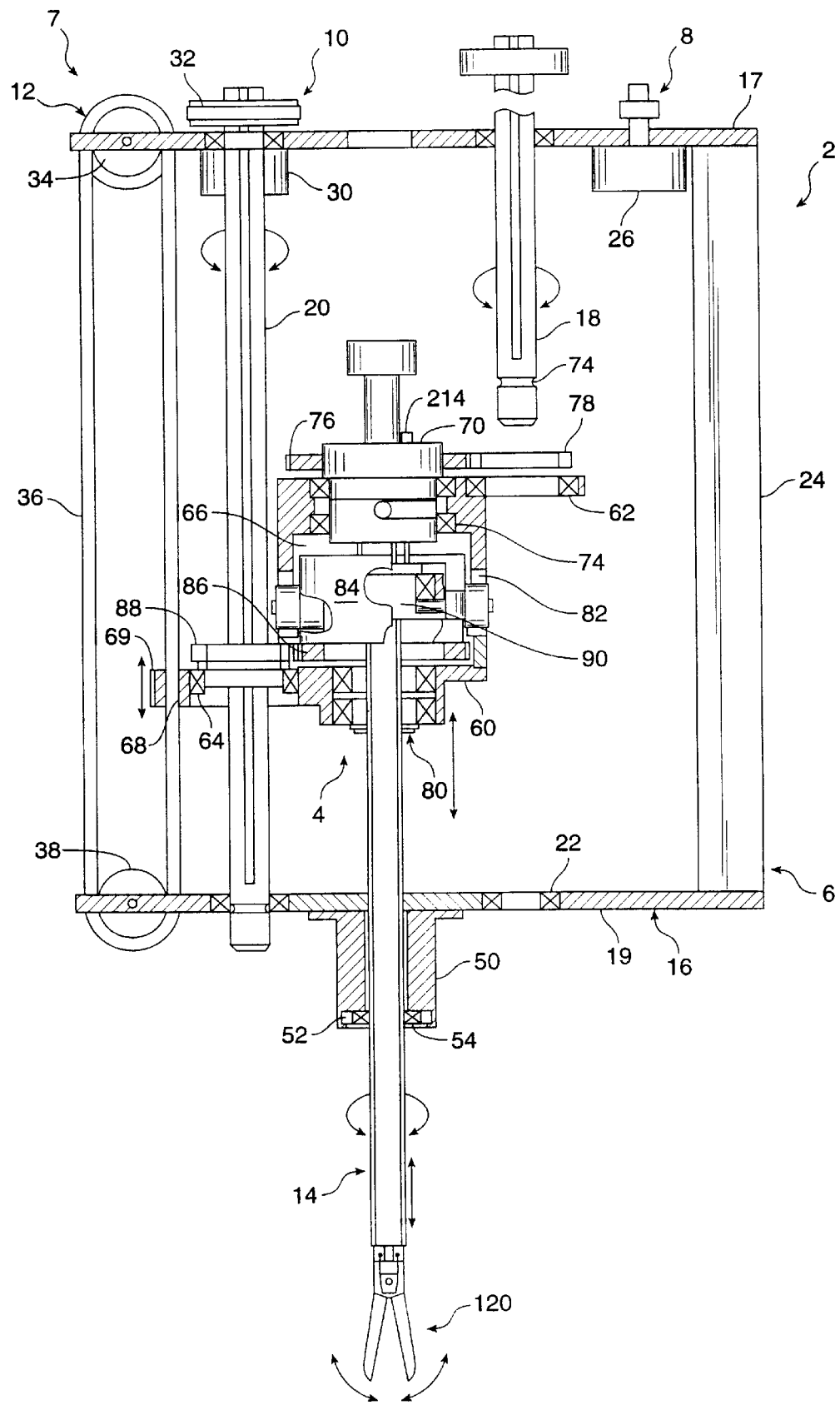
FIG. 1A is a partial sectional elevational view of the manipulator assembly of FIG. 1 illustrating the removal of an instrument holder from the rest of the assembly.
Figure 7:
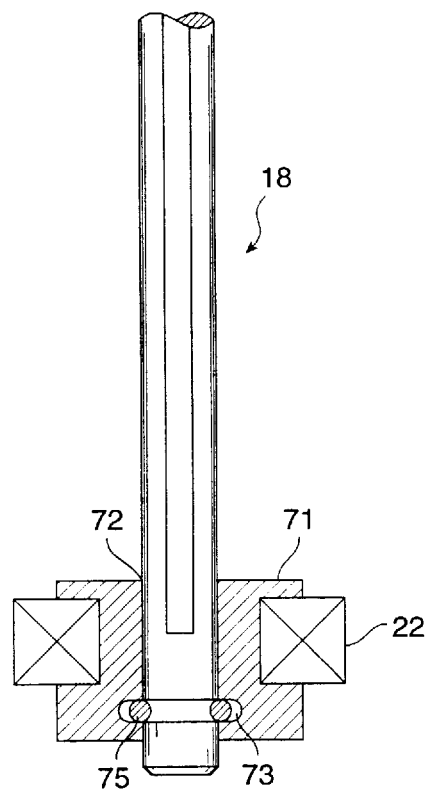
FIG. 7 is an enlarged detail of a portion of the frame of the manipulator assembly of FIG. 1 illustrating a coupling mechanism for removing the shafts from the frame.

Instrument holder 4 is removably coupled to base 6 and the drive motors so that the entire holder 4 can be removed and sterilized by conventional methods, such as steam, heat and pressure, chemicals, etc. In the preferred configuration, arm 68 includes a toggle switch 69 that can be rotated to release arm 68 from drive belt 36 (FIG. 1). In addition, shafts 18, 20 are removably coupled to bearings 22 so that the shafts can be axially withdrawn from support members 17, 19 of frame 16, as shown in FIG. 1A. To this end, the distal bearings 22 preferably include a coupling mechanism for allowing the removal of shafts 18, 20. As shown in FIG. 7, distal support member 19 includes a support collar 71 within each distal bearing 22 having an inner bore 72 for passage of one of the shafts 18, 20. Each support collar 71 has an internal groove 73 and shafts 18, 20 each have an annular groove 74 (see FIG. 1A) near their lower ends that is aligned with internal grooves 73 when the shafts are suitably mounted within frame 16 (FIG. 1). A spring clip 75 is positioned within each internal groove 73 to hold each shaft 18, 20 within the respective support collar 71. Spring clip 74 has a discontinuity (not shown) to allow removal of shafts 18, 20 upon the application of a threshold axial force on the shafts.

To remove instrument holder 4 from base 6, the operator rotates toggle switch 69 to release arm 68 from drive belt 36 and removes drive belts 28, 32 from drives 8, 10. As shown in FIG. 1A, the operator holds instrument holder 4 and pulls shafts 18, 20 upwards, providing enough force to release spring clips 75. Shafts 18, 20 will disengage from distal bearings 22 and slide through ball-spline bearings 62, 64 so that instrument holder 4 is disconnected from base 6. It should be understood that the invention is not limited to the above described means for removably coupling instrument holder 4 to base 6 and drive assembly 7. For example, distal support member 19 may be removably coupled to the rest of frame 16 so that the surgeon simply removes member 19 and slides holder down and off shafts 18, 20. Proximal support member 17 may be removably coupled to frame 16 in a similar manner. Alternatively, the drive motors may be housed in a separate servo-box (not shown) that is removably attached to base 6. In this configuration, the servo-box would be removed from base 6 so that the entire base 6, together with holder 4, can be sterilized.

The lower portion of base 6 (including distal support member 19) may also be sterilized to decontaminate those parts that come into contact with holder 4 or instrument 14 (e.g., by dipping the lower portion of base 6 into a sterilizing bath). To facilitate this type of sterilization, shafts 18, 20 will preferably be somewhat longer than shown in FIG. 1 so that the upper portion of base 6, including drive assembly 7, is disposed sufficiently away from holder 4 and instrument 14. In this manner, the surgical manipulator can be easily sterilized after a surgical procedure without damaging the drive motors or the electrical connections required for the telerobotic system.

Instrument holder 4 further includes an instrument support 70 (see detail in FIG. 3A), for releasably coupling surgical instrument 14 to the manipulator assembly. Instrument support 70 is rotatably mounted within chassis 60 via mounting bearings 74 so that support 70 and the instrument can be rotated therein. As shown in FIG. 1, support 70 is circumscribed by an annular ring gear 76 having teeth that mesh with the teeth of a drive gear 78 mounted to first shaft 18. Drive gear 78 is configured around first shaft 18 such that it will rotate with first shaft 18, thereby rotating instrument support 70 and the surgical instrument therewith. Drive gear 78 is also configured to move axially with respect to first shaft 18 to allow axial movement of instrument holder 4 with respect to frame 16.

Instrument holder 4 further includes an actuator driver 80 (see detail in FIG. 5) movably mounted within axial guide slots 82 on either side of chassis 60. Actuator driver 80 comprises a helical actuator 84 (see detail in FIG. 6B) having a ring gear 86 that meshes with a gripper drive gear 88 mounted to second shaft 20. Rotation of second shaft 20 causes rotation of gripper drive gear 88, thereby rotating ring gear 86 and helical actuator 84 within chassis 60. Actuator driver 80 further includes an actuator carriage assembly 90 (see detail in FIG. 6A) for releasably coupling an end effector actuator of surgical instrument 14 to instrument holder 4 (see FIG. 2). carriage assembly 90 is mounted within helical actuator 84 and chassis 60 such that rotation of helical actuator 84 causes a corresponding axial movement of carriage assembly 90 with respect to chassis 60, as discussed in greater detail below.

Figure 2A:
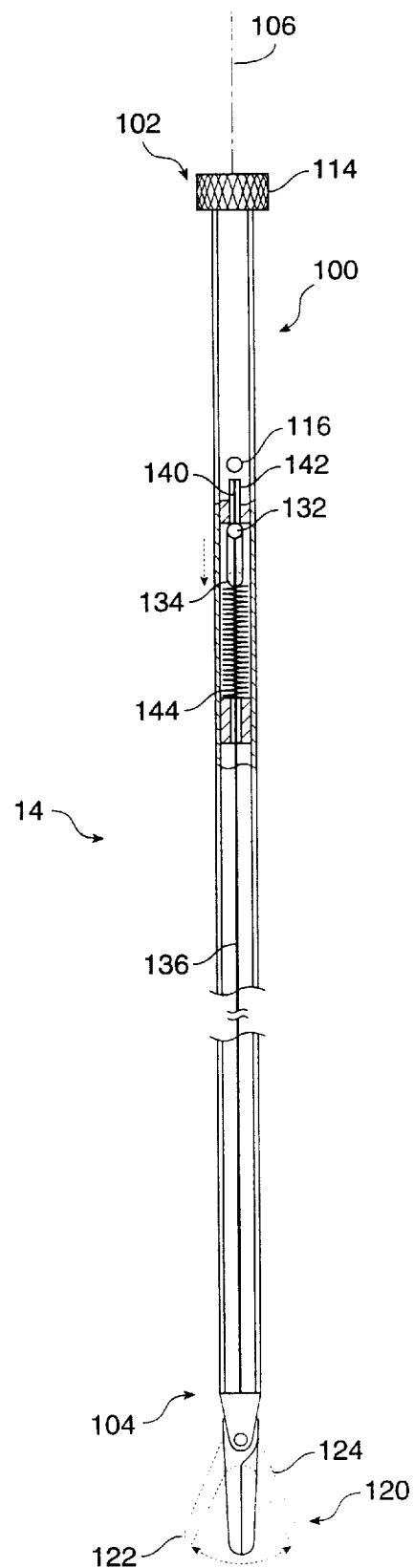
FIGS. 2A and 2B are enlarged side and front cross-sectional views, respectively, of the surgical instrument of FIG. 1.
Figure 2B:
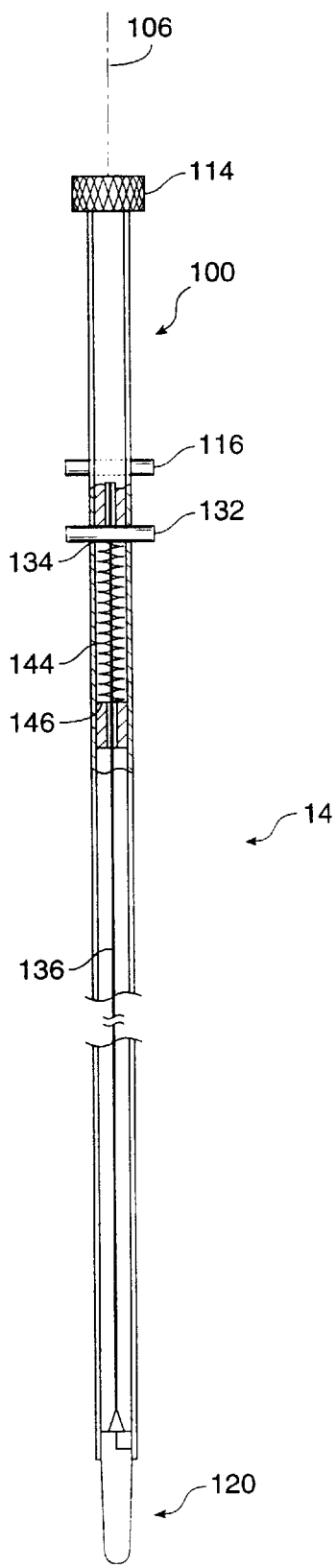

FIGS. 2A and 2B illustrate a specific embodiment of an endoscopic surgical instrument 14 capable of being operated by a motorized manipulator, such as manipulator assembly 2, for telerobotic surgery. Surgical instrument 14 can be a variety of conventional endoscopic instruments adapted for delivery through a percutaneous penetration into a body cavity, such as tissue graspers, needle drivers, microscissors, electrocautery dissectors, etc. In the preferred embodiment, instrument 14 is a tissue grasper comprising a shaft 100 having a proximal end 102, a distal end 104 and a longitudinal axis 106 therebetween. A knurled handle 114 is attached to proximal end 102 of shaft 100 to facilitate manipulation of instrument 14.

Shaft 100 is preferably a stainless steel tube having an outer diameter in the range of 2–10 mm, usually 4–8 mm, so as to fit within a cannula having an internal diameter in the range of 2–15 mm. Shaft 100 can also be introduced directly through a percutaneous incision in the patient. Shaft 100 has a length selected to reach a target site in a body cavity, such as the abdomen, and to extend sufficiently out of the body cavity to facilitate easy manipulation of surgical instrument 14. Thus, shaft 100 should be at least between 10 cm and 40 cm and is preferably between 17 cm and 30 cm. It should be noted that although shaft 100 is shown as having a circular cross-sectional shape in the drawings, shaft 100 could alternatively have a rectangular, triangular, oval or channel cross-sectional shape.

In a specific configuration, shaft 100 includes a mounting means for releasably coupling surgical instrument 14 to instrument support 70 and first drive 8 of manipulator assembly 2. In the preferred embodiment, mounting means comprises a pair of opposed mounting pins 116 extending laterally outward from shaft 100. Mounting pins 116 are rigidly connected to shaft 100 and are adapted for engaging a twist-lock interface on instrument support 70, as discussed in detail below. It should be understood that the invention is not limited to a pair of opposing pins and mounting means can include a single mounting pin or a plurality of pins extending circumferentially around shaft. Alternatively, pins 116 may have a variety of other shapes, such as spherical or annular, if desired.

Instrument 14 includes an end effector 120 extending from distal end 104 for engaging a tissue structure on the patient, such as the abdomen during laparoscopic surgery. In the preferred embodiment, end effector 120 comprises a pair of jaws 122, 124 that are movable between open and closed positions for grasping a blood vessel, holding a suture, etc. Jaws 122, 124 preferably have transverse grooves or other textural features (not shown) on opposing surfaces to facilitate gripping of the tissue structure. To avoid the possibility of damaging the tissue to which jaws 122, 124 are applied, the jaws may also include atraumatic means (not shown), such as elastomeric sleeves made of rubber, foam or surgical gauze wrapped around jaws 122, 124.

Figure 4:
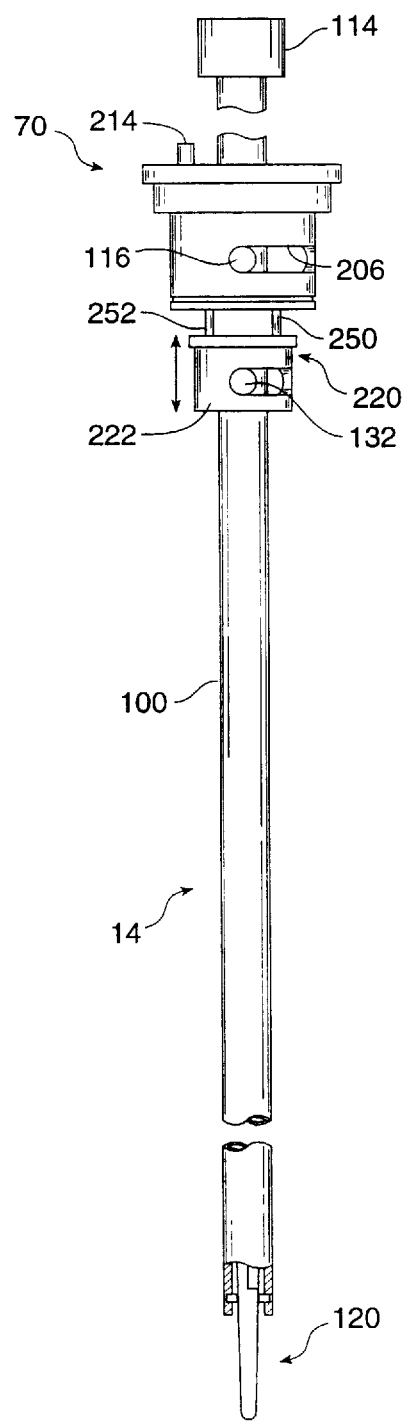
FIG. 4 is a front elevational view of the surgical instrument mounted within the instrument support and actuator pin catch of FIGS. 3A and 3B.

To move jaws 122, 124 between the open and closed positions, instrument 14 includes an end effector actuator releasably coupled to actuator driver 80 and second drive 10 of manipulation assembly 2 (see FIG. 4). In the preferred embodiment, end effector actuator comprises a pair of opposed actuator pins 132 laterally protruding from axially extending slots 134 in shaft 100. Actuator pins 132 are coupled to an elongate rod 136 slidably disposed within an inner lumen 138 of shaft 100. Actuator pins 132 are slidable within slots 134 so that rod 136 is axially movable with respect to shaft 100 and mounting pins 116 to open and close jaws 122, 124, as is conventional in the art. Elongate rod 136 has a proximal portion 140 that is disposed within an inner lumen 142 within shaft 100 to prevent actuator pins 132 from moving in the lateral direction and to ensure that rod 136 remains generally centered within shaft 100 during a surgical procedure.

Jaws 122, 124 are preferably biased into the closed positioned by an annular compression spring 144 positioned within shaft 100 between actuator pins 132 and an annular disc 146 fixed to the inside surface of shaft 100. During endoscopic procedures, this allows the surgical team to introduce jaws 122, 124 through cannula 50 (or any other type of percutaneous penetration) and into the body cavity without getting stuck within cannula 50 or damaging surrounding tissue.

Figure 3A:
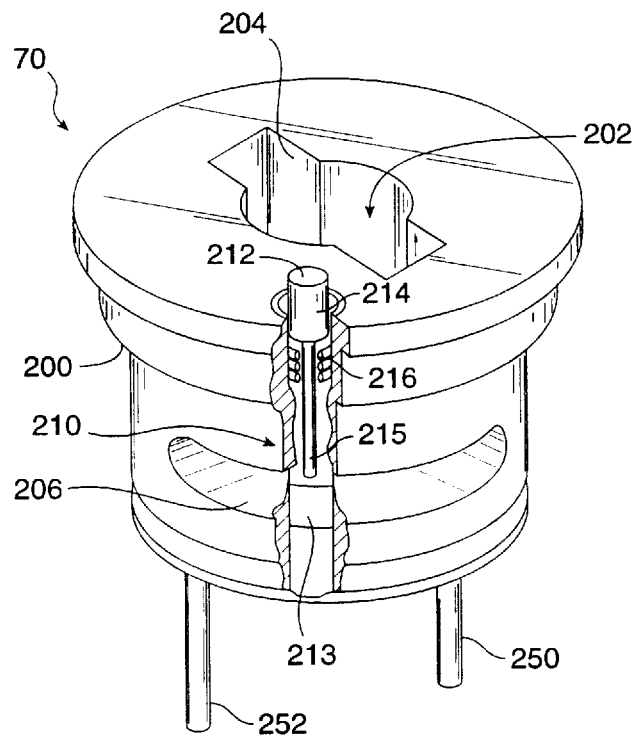
FIGS. 3A and 3B are perspective views of an instrument support and an actuator pin catch, respectively, for releasably mounting the surgical instrument to the manipulator assembly.
Figure 3B:
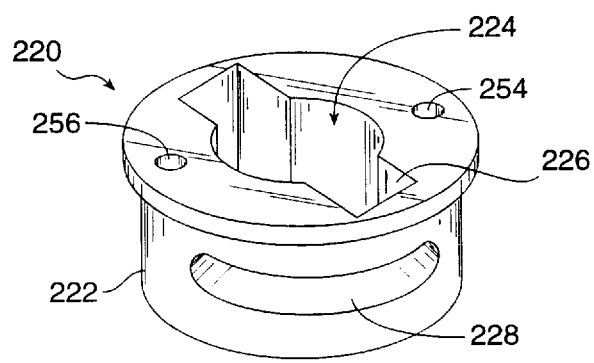

FIGS. 3A, 3B and 4 illustrate a twist lock mechanism for releasably connecting surgical instrument 14 to manipulator assembly 2 so that different instruments may be rapidly changed during an endoscopic surgical procedure. As shown in FIG. 3A, instrument support 70 comprises an annular collar 200 defining a central bore 202 for receiving shaft 100 of surgical instrument 14. Collar 200 further defines an axially extending slot 204 in communication with bore 202 and sized to allow mounting and actuator pins 116, 132 of instrument 14 to slide therethrough (see FIG. 4). Two locking slots 206 are cut into annular collar 200 at a transverse angle, preferably about 90°, to axially extending slot 204 (note that only one of the locking slots are shown in FIG. 3A). Locking slots 206 intersect slot 204 near the center of annular collar 200 and extend circumferentially around bore 202, preferably about 90°, to allow rotation of both mounting pins 116 therethrough, as discussed below.

Figure 8:
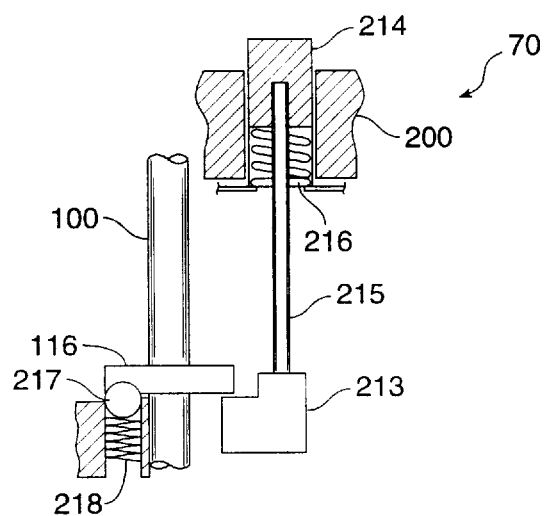
FIG. 8 is a partial cross-sectional view of the instrument support of FIG. 3A illustrating a locking mechanism for a twist lock interface according to the present invention.

As shown in FIGS. 3A and 8, instrument support 70 further comprises means for locking mounting pins 116 into locking slots 206 so that the instrument cannot be accidently twisted and thereby disengaged from instrument support 70 during surgery. Preferably, the locking means comprises a latch assembly having a plunger 210 slidably disposed within a hole 212 in collar 200, as shown in FIG. 3A. Plunger 210 comprises an L-shaped latch 213 coupled to a release button 214 by a rod 215 extending through hole 212. Plunger 210 is movable between a first position, where latch 213 is not disposed within locking slots 206 so that mounting pins 116 are free to rotate therethrough, and a second position, where latch 213 is at least partially disposed within one of the locking slots 206 so as to prevent rotation of mounting pins 116. Latch 213 is preferably biased into the second or locked position by a compression spring 216.

Button 214 is disposed on the upper surface of support 70 for manual actuation by the surgeon or automatic actuation by base 6. Preferably, when instrument holder 4 is moved to its most proximal position (see FIG. 1), proximal support member 17 of frame 16 depresses release switch 214 to move latch 213 into the first or open position. With this configuration, instruments can be exchanged only when the instrument holder 4 is in the most proximal position, where shaft 100 of instrument 14 is easily accessible. In addition, this prevents the accidental release of the instrument when its distal end has penetrated cannula 50 and is disposed within the body cavity.

The intersecting axial and locking slots 204, 206 form an interface for releasably coupling mounting pins 116 of surgical instrument 14 to instrument holder 4. To insert instrument 14, the surgeon aligns mounting pins 116 with axial slot 204 and slides the instrument through bore 202 of annular collar 200 until mounting pins 116 are aligned with locking slots 206, as shown in FIG. 4. The instrument is then rotated a sufficient distance, preferably about a ¼ turn, through locking slots 206 so that the pins are no longer aligned with axial slot 204. When instrument 14 is moved distally, switch 214 is released (FIG. 1) and latch 213 moves into locking slots 206 to prevent mounting pins 116 from rotating back into alignment with axial slot 204 so that instrument 14 is secured to instrument support 70. It should be noted that a single mounting pin may be utilized with the above described configuration to lock the surgical instrument to the support. However, two opposing pins are preferred because this configuration reduces torsional forces on the inner surface of locking slots 206.

As shown in FIG. 8, the locking means preferably includes a ball detent 217 disposed within collar 200. Ball detent 217 is biased upward into one of the locking slots 206 by a spring 218. Ball detent 217 serves to temporarily capture mounting pins 116 in a position rotated about 90° from alignment with axial slot 204. This ensures that the mounting pins will be completely rotated into the proper position (i.e., out of the way of latch 213) when instrument 14 is twisted into instrument holder. Otherwise, when switch 214 is released, latch 213 could become engaged with mounting pins 216 so that the latch is unable to move completely into the locked position, thereby potentially causing the accidental release of instrument 14 during surgery.

Figure 5:
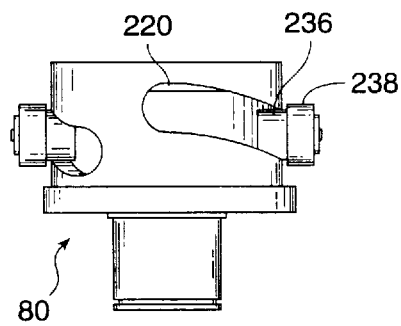
FIG. 5 is a front elevational view of an actuator driver for providing axial movement of the actuator pin catch of FIG. 3B.

As shown in FIGS. 3B, 4 and 5, actuator driver 80 of instrument holder 4 further comprises an actuator pin catch 220 for releasably holding and moving actuator pins 132 of instrument 14. Actuator pin catch 220 is constructed similarly to instrument support 70 (FIG. 3A), comprising an annular collar 222 that defines a bore 224 for receiving shaft 100 and an axially extending slot 226 for receiving actuator pins 132. A locking slot 228 is cut into actuator pin catch 220 at a 90° angle so that actuator pins can be rotated into the lock slot to couple actuator pins 132 to actuator driver 66, as discussed above in reference to the mounting pins. It should be noted that slot 226 need not extend completely through collar 222 since actuator pins 132 are located distally of mounting pins 116 (the instrument is preferably inserted jaws first). Of course, actuator and mounting pins 132, 116 may be reversed so that the mounting pins are distal to the actuator pins, if desired.

Figure 6A:
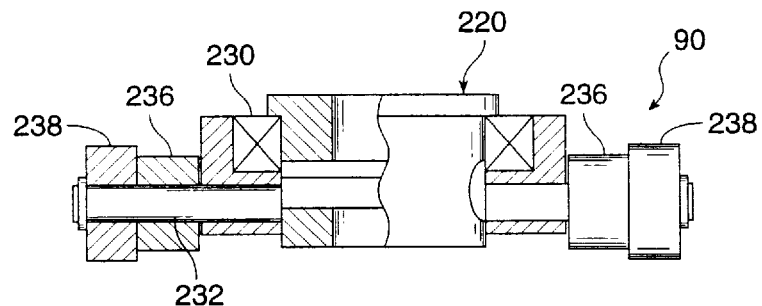
FIGS. 6A and 6B are enlarged cross-sectional views of an actuator carriage assembly and a helical actuator of the actuator driver of FIG. 5.

Referring to FIG. 6A, actuator pin catch 220 is rotatably mounted on a ball bearing 230 in actuator carriage assembly 90. Bearing 230 allows the pin catch 220 to rotate freely in carriage assembly 90 while preventing relative axial motion. Therefore, when instrument 14 is rotated by first drive 8, actuator pins 132 will rotate within carriage assembly 90. Carriage assembly 90 further comprises two sets of axles 232 for rotatably supporting a pair of inner rollers 236 and a pair of outer rollers 238. As shown in FIG. 1, outer rollers 238 are slidably disposed within axial guide slots 82 of chassis 60 to prevent rotation of carriage assembly 90 with respect to chassis 60. Inner and outer rollers 236, 238 cooperate with helical actuator 84 and chassis 60 of instrument holder 4 to move axially with respect to the holder, thereby axially moving pin catch 220 and actuator pins 132 therewith relative to shaft 100 of instrument 14 (which actuates jaws 122, 124, as discussed above).

Figure 6B:
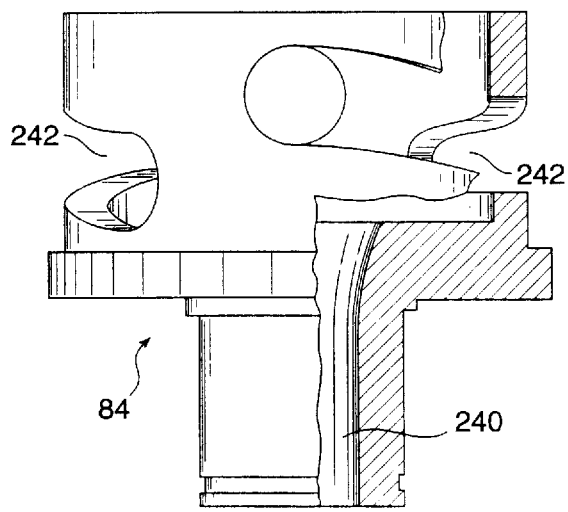

As shown in FIG. 6B, helical actuator 84 includes a central bore 240 for receiving carriage assembly 90 and surgical instrument 14 and two opposing helical tracks 242, 244 each extending circumferentially around helical actuator 84 (preferably slightly less than 180°) for receiving inner rollers 236 of carriage assembly 90, as shown in FIG. 5. With outer rollers 238 constrained in axial guide slots 82 of chassis 60, rotation of helical actuator 84 causes carriage assembly 90 (and actuator pin catch 220) to move up or down, depending on the sense of the rotation. Because of the symmetrical design of helical actuator 84, the actuation force applied by second driver 10 will not generate any effective side loads on instrument 14, which avoids frictional coupling with other degrees of freedom such as axial (third driver 12) and rotation (first driver 8). In the preferred embodiment, helical tracks 242, 244 have a pitch selected such that the mechanism can be easily back-driven, allowing grip forces to be sensed in a position-servoed teleoperation system.

As shown in FIGS. 3A and 3B, instrument holder 4 further includes a pair of axial guide pins 250, 252 fixed to instrument support 70. Actuator pin catch 220 has a pair of openings 254, 256 for receiving guide pins 250, 252. Guide pins 250, 252 prevent relative rotation between pin catch 220 and support 70 (so that actuator and mounting pins 116, 132 can both rotate with the instrument) and allow axial movement relative to each other (so that end effector 120 can be actuated by axial movement of actuator pins 132).

Figure 9:
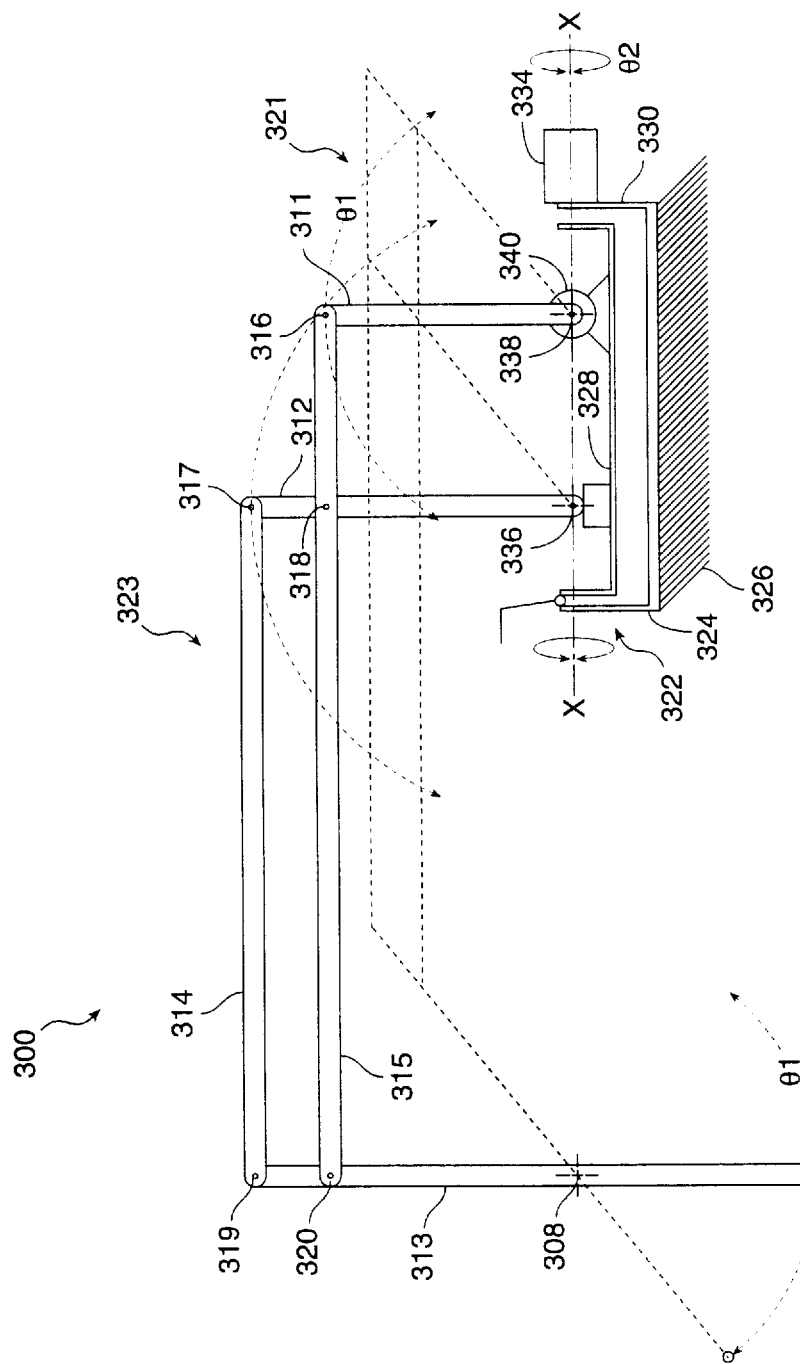
FIG. 9 is an elevational view of a remote center positioner for holding the manipulator assembly of FIG. 1.

FIG. 9 is an elevational view of a remote center positioner 300 which can be used to support manipulator assembly 2 above the patient (note that support manipulator 2 is not shown in FIG. 8). Remote center positioner 300 provides two degrees of freedom for positioning manipulator assembly 2, constraining it to rotate about a point 308 coincident with the entry incision. Preferably, point 308 will be approximately the center of bearing 54 in cannula 50 (FIG. 1). A more complete description of remote center positioner 300 is described in commonly assigned co-pending application Ser. No. 08/062,404 filed May 14, 1993 REMOTE CENTER POSITIONER now abandoned, which is incorporated herein by reference.

A first linkage means is indicated generally by the numeral 321 and a second linkage in the form of a parallelogram is indicated by the numeral 323. The first linkage means is pivotally mounted on a base plate for rotation about an x—x axis. The second linkage means is pivotally connected to the first linkage means and is adapted to move in a plane parallel to the first linkage. Five link members (including extensions thereof), 311, 312, 313, 314, and 315 are connected together with pivot joints 316–320. A portion of element 313 extends beyond pivot 320 of the parallelogram linkage. The parallelogram linkage has an operating end at link member 313 and a driving end at link member 312. The elongated element 313 may, as desired later, carry a surgical instrument or other device, such as support bracket 24 of manipulator assembly 2. The pivot joints allow relative motion of the link members only in the plane containing them.

A parallelogram linkage is formed by corresponding link members 314, 315 and link members 312 and 313. The portions of link members 314 and 315 of the parallelogram are of equal length as are the portions of members 312 and 313 of the parallelogram. These members are connected together in a parallelogram for relative movement only in the plane formed by the members. A rotatable joint generally indicated by the numeral 322 is connected to a suitable base 324. The rotatable joint 322 is mounted on a base plate 326 adapted to be fixedly mounted to the base support means 324. A pivot plate 328 is pivotally mounted to base plate 326 by suitable means at, such as, pivots 330, 332. Thus pivot plate 328 may be rotated about axis x—x through a desired angle Θ2. This may be accomplished manually or by a suitable pivot drive motor 334.

A first linkage is pivotally mounted on the pivot plate 328 of the rotatable joint 322. The linkage elements 311, 312 and the link members are relatively stiff or inflexible so that they may adequately support an instrument used in surgical operations. Rods made of aluminum or other metal are useful as such links. The linkage elements 311 and 312 are pivotally mounted on base plate 328 for rotation with respect to the rotatable joint by pivots 336 and 338. At least one of the pivots 336, 338 is positioned so that its axis of rotation is normal to and intersects the x—x axis. Movement may occur manually or may occur using a linkage drive motor 340. The first linkage is also shaped in the form of a parallelogram formed by linkage elements 311, and 312; the portion of link member 315 connected thereto by pivots 316, 318; and base plate 328. One of the link members 315 is thus utilized in both the first 321 and second 323 linkage means. Linkage element 312 also forms a common link of both the first linkage means 321 and the second linkage means 323. In accordance with the invention, a remote center of spherical rotation 308 is provided by the above described embodiment of apparatus when the linkage element 311 is rotated and/or when pivot plate 328 is rotated about axis x—x. Thus, the end of element 313 can be moved through desired angles Θ1 and Θ2 or rotated about its own axis while the remote center of rotation remains at the same location.

FIG. 9 also shows an inclinometer (not shown) attached to the base of remote center positioner 300. The remote center positioner may be mounted at an arbitrary orientation with respect to vertical depending on the particular surgery to be performed, and inclinometer (not shown) can be used to measure this orientation. The measured orientation can be used to calculate and implement servo control signals necessary to control the telerobotic system so as to prevent gravitational forces acting on the system mechanisms from being felt by the surgeon.

Variations and changes may be made by others without departing from the spirit of the present invention. For example, it should be understood that the present invention is not limited to endoscopic surgery. In fact, instrument holder 4, along with a telerobotic control mechanism, would be particularly useful during open surgical procedures, allowing a surgeon to perform an operation from a remote location, such as a different room or a completely different hospital.

What is claimed is:

1. An apparatus for manipulating a surgical instrument in a sterile surgical field comprising:
    a support base fixable to a surface;
    a sterilizable instrument holder movably mounted on said support base and adapted to releasably hold the surgical instrument, the instrument holder comprising:
        a body; and
        an instrument support movably mounted on said body and having an interface engageable with the surgical instrument to releasably mount the instrument to said instrument holder;
    a drive assembly operatively coupled to said instrument holder for providing said instrument with at least two degrees of freedom, said drive assembly comprising:
        a first controllable motor operatively connected to move said instrument support; and
        a second controllable motor operatively connected to move said instrument holder body relative to said support base;
    a coupling mechanism for removably attaching said instrument holder to said support base and said drive assembly, wherein said instrument holder is separable from said support base and said drive assembly for sterilization of said instrument holder between surgical procedures;
    wherein said support base comprises first and second spaced support shafts and said instrument holder comprises first. and second mounts slidably mounted to the first and second support shafts;
    wherein said instrument holder body further includes an arm removably coupled to said second controllable motor for axial movement of said first and second mounts along said first and second support shafts thereby moving said instrument in an axial, direction;
    wherein said support base comprises a frame having distal and proximal elongate support members, said first and second shafts each having first and second ends rotatably supported within said distal and proximal support members;
    wherein said coupling mechanism comprises a disconnecting means for separating said spaced support shafts from said support base to allow said instrument holder to be removed from said support base and said drive assembly; and
    wherein said disconnecting means comprises an annular groove in each of the spaced support shafts and an internal grove in each of said mounts in communication with said annular groove, said disconnecting means further including a spring clip positioned within said annular and internal grooves so to prevent axial movement of said shafts relative to said mounts, said spring clip having an opening for allowing release of said shafts from said mounts when a threshold axial forces is applied to said shafts.

2. An instrument holder adapted to be driven by a drive assembly coupled to a robotic control mechanism for manipulation of a surgical instrument of the type having a shaft with an axially fixed mounting means, an end effector and a movable end effector actuator, the instrument holder comprising:
    a body having an axial passage for receiving said instrument and at least one mount for movably coupling said body to the drive assembly;
    an instrument support having an axial passage for receiving said instrument and a first interface engageable with the axially fixed mounting means of the instrument for releasably mounting the instrument to said instrument holder, said instrument support being rotatably coupled to said body and having a first coupling structured and arranged to connect said instrument support to the drive assembly for rotating said instrument;
    an actuator driver having an axial passage for receiving said instrument, a second interface engageable with the end effector actuator of the instrument and a second coupling for connecting said actuator driver to the drive assembly, said actuator driver further comprising means for translating rotational movement of the second coupling into axial displacement of the second interface relative to said body to actuate the end effector of the instrument.

3. The holder of claim 2 wherein said translating means comprises a first portion rotatably mounted to said body and a second portion axially movable with respect to said body, said first portion being coupled to said second portion such that rotation of said first portion causes axial displacement of said second portion and the second interface therewith.

4. The holder of claim 3 wherein said second coupling is an annular gear member structured and arranged for coupling to a motor shaft for rotation of said first portion of said actuator driver.

5. The holder of claim 3 wherein said second portion of said actuator driver comprises a carriage assembly movably mounted to said body and an annular collar releasably coupled to said end effector actuator of said instrument and rotatably coupled to said actuator carriage assembly.

6. The holder of claim 5 wherein said body includes opposing axial slots, said carriage assembly including a first pair of rotatable members disposed within said axial slots to prevent rotation of said actuator carriage assembly with respect to said instrument holder and to allow axial movement with respect to said holder.

7. The holder of claim 6 wherein said carriage assembly further includes a second pair of rotatable members disposed radially inward from said first pair of rotatable members, said first portion of said actuator driver comprising a concentric helical actuator with a pair of helical slots for receiving said second pair of rotatable members so that rotation of said helical actuator axially displaces said carriage assembly and said annular collar with respect to said instrument holder.

8. The holder of claim 2 wherein said first coupling comprises an annular gear member structured and arranged for coupling to a motor shaft for rotation of said instrument support.

* * * * *

UNITED STATES PATENT AND TRADEMARK OFFICE
CERTIFICATE OF CORRECTION

PATENT NO.    : 5,807,378
DATED         : September 15, 1998
INVENTOR(S)   : Joel F. Jensen and John W. Hill Page 1 of 1

It is certified that error appears in the above-identified patent and that said Letters Patent is hereby corrected as shown below:

<u>Column 1,</u>
Line 7, please add

-- STATEMENT AS TO RIGHTS TO INVENTIONS MADE UNDER FEDERALLY SPONSORED RESEARCH OR DEVELOPMENT

The invention was made with Government support under Grant Number 5 R01 GM 44902-2 awarded by National Institute of Health. The Government has certain rights in this invention." --

Signed and Sealed this

Twenty-ninth Day of April, 2003

JAMES E. ROGAN
*Director of the United States Patent and Trademark Office*